US008623283B2

(12) United States Patent
Van Breemen et al.

(10) Patent No.: US 8,623,283 B2
(45) Date of Patent: Jan. 7, 2014

(54) COMBINED ELECTRICAL AND OPTICAL SENSOR FOR FLUIDS

(75) Inventors: Albert Jos Jan Marie Van Breemen, Eindhoven (NL); Harmannus Franciscus Maria Schoo, Eersel (NL)

(73) Assignee: Nederlandse Organisatie voor toegepast-natuurwetenschappelijk onderzoek TNO, Delft (NL)

( * ) Notice: Subject to any disclaimer, the term of this patent is extended or adjusted under 35 U.S.C. 154(b) by 719 days.

(21) Appl. No.: 12/668,235

(22) PCT Filed: Jul. 9, 2008

(86) PCT No.: PCT/NL2008/050461
§ 371 (c)(1),
(2), (4) Date: Sep. 23, 2010

(87) PCT Pub. No.: WO2009/008721
PCT Pub. Date: Jan. 15, 2009

(65) Prior Publication Data
US 2011/0025351 A1    Feb. 3, 2011

(30) Foreign Application Priority Data
Jul. 9, 2007   (EP) .................................... 07112041

(51) Int. Cl.
  *G01N 21/00*   (2006.01)

(52) U.S. Cl.
  USPC ........ 422/82.05; 422/82.02; 324/96; 324/693

(58) Field of Classification Search
  None
  See application file for complete search history.

(56) References Cited

U.S. PATENT DOCUMENTS

2003/0215891 A1   11/2003   Bickel et al.
2005/0046429 A1    3/2005   Gruebler et al.

FOREIGN PATENT DOCUMENTS

DE   20007376   8/2000
EP   0116094    8/1984

OTHER PUBLICATIONS

International Search Report, Application No. PCT/NL2008/050461, mailed Dec. 10, 2008.
Fritzsche et al.; "Metal nanoparticles as labels for heterogeneous, chip-based DNA detection"; Nanotechnology; vol. 14, No. 12, Sep. 17, 2003; pp. R63-R73.

*Primary Examiner* — Robert Xu
(74) *Attorney, Agent, or Firm* — Renner, Otto, Boisselle & Sklar, LLP

(57) ABSTRACT

The present invention relates to a sensor for the detection of an analyte, comprising a fluid holder (8), an optical detection system (3, 9) for carrying out an optical detection at the fluid holder (8) and an electrical detection system (4) for measuring electric conductivity or resistance inside the fluid holder (8) and to a method comprising the use of such a sensor.

9 Claims, 3 Drawing Sheets

COMBINED ELECTRICAL AND OPTICAL SENSOR FOR FLUIDS

This application is a national phase of International Application No. PCT/NL2008/050461 filed Jul. 9, 2008.

The invention relates to a sensor for the detection of an analyte and to a method for detecting an analyte.

In Nanoletters 2005, Vol 5, No. 7, pp 1475-1482, Möller et al. report that sensors making use of electrical resistance for the detection of biomolecules, such as DNA, form an interesting alternative to sensors making use of fluorescence detection. A method is described wherein enzyme or nanoparticle labels are used in combination with metal enhancement (deposition) to detect DNA. The labels serve as a nucleation site or catalyse silver deposition in order to bridge a gap between two metal electrodes. The enhancement time until a characteristic drop in resistance can be detected, is a measure for the amount of the DNA. Advantages of such detection technique over conventional fluorescence detection are the ease of miniaturisation and the relatively low cost. However, the method described, has some drawbacks. In practice, it is generally not feasible to monitor the electrical resistance with satisfactory accuracy during enhancement in real time (on-line), because generally a sufficient change in the electrical signal to be used for analytical purposes is observed only after the gap between the electrodes is fully closed by the silver layer. Thus, no real-time information during the enhancement (as the gap is reduced in size) is collected.

Thus, in practice, silver enhancement is allowed to continue for a specific period of time. Then the detection cell (comprising the electrodes and—if present a deposition between the electrodes) is washed and dried, and thereafter the electrical resistance between the electrodes (between which silver is deposited if an analyte of interest is present) is measured. If the period of time is not sufficient to let sufficient deposition be formed between the electrodes to form a conductive path (the percolation threshold), a further enhancement step is required, before the analysis is completed. Thus, the method may be tedious. Further, it is contemplated that the need to repeat enhancement, washing and drying may make the method less robust.

Further publications describing detection by electrical resistance are Diessel et al. Biosensors and Bioelectronics (2004) 1229-1235, US 2003/0087277A1, WO 2005/003772 A1 and WO 00/39325.

It is an object of the present invention to provide a novel sensor for the detection of an analyte, comprising an electrical detection system for measuring electric conductivity or resistance.

It is a further object to provide such a novel sensor which overcomes one or more problems experienced with known electrical detection systems, such as described above.

It is a further object to provide a sensor having an improved reliability.

One or more other objects which may be solved in accordance with the invention will be apparent from the description and/or claims, below.

It has now been found that a sensor comprising an electrical detection system for measuring electric conductivity or resistance can be provided with at least one further detection system in that thus one or more of said objects can be realised.

Accordingly, the present invention relates to a sensor for the detection of an analyte, comprising a fluid holder, an optical detection system for carrying out an optical detection at the fluid holder and an electrical detection system for measuring electric conductivity or resistance inside the fluid holder.

The invention further relates to a method for detecting an analyte, comprising applying a sample—and if desired applying one or more reagents, such as one or more reagents selected from the group of labels, probes, enzymes, metal ions, reducing agents, metal nanoparticles together with applying the sample or separate from applying the sample—to a fluid holder of a sensor according to the invention, measuring an optical property in the fluid holder—such as UV-absorbance, VIS-absorbance, IR-absorbance, fluorescence, phosphorescence, photoluminescence, refractive index—with the optical detection system and measuring the conductivity or resistance with the electrical detection system.

The fluid holder 8 may in principle be any container suitable for holding a sample, and if desired, reagents, washing fluids and the like. In particular the fluid holder 8 may be part of an array of detection cells 14, e.g. of a (miniature) microtitre plate or the like. The term "detection cell" is used herein for a part of the sensor comprising an area (/volume) for containing an analyte (in the sample or immobilised to a specific probe), at least two electrodes between which electrical resistance/conductivity can be measured (in general spatially apart such that the space defines the area/volume wherein analyte may be contained), a light source capable of emitting electromagnetic radiation (light) directed to the area/volume and a photodetector capable of measuring electromagnetic radiation (light) passed to, reflected from or emitted from the area/volume which may contain the sample.

The sensor or at least the fluid holder, optical detection system and electrical detection system may in particular be or form part of a microstructured device, such as an assembly of a read-out system 1 (in particular a printed circuit board with a module to calculate and preferably also show results of a measurement), a microfluidic device (wherein the fluid can be held) 8, provided with an array 4 of detection cells 14 for determining conductivity/resistance, positioned between a light source 10, such as one or more light emitting diodes (LED's), which may be structured to form an array, and an array of detection photodiodes 5, wherein the LEDs are preferably organic LEDs and the detection photodiodes are preferably organic photodiodes. If desired, multiple LED's can be provided and arranged such that each LED provides a light source for a single detection cell 14.

The analyte can in principle be any molecule of interest. The analyte preferably is a biomolecule, in particular a biomolecule selected from nucleotides, including oligonucleotides and polynucleotides; peptides, including oligopeptides, polypeptides and proteins; hormones; carbohydrates; and vitamins. A sensor according to the invention may in particular be used for in vitro or in vivo diagnosing or screening for a medical disorder, for quantitatively or qualitatively determining the presence of an analyte in a body fluid or body tissue, for quantitatively or qualitatively determining the presence of an analyte in an agricultural product, for quantitatively or qualitatively determining the presence of an analyte in a food, a drink or for quantitatively or qualitatively determining the presence of an analyte in water, in particular in drinking water.

FIG. 1 schematically shows a 3D view of a (disassembled) sensor according to the invention.

Figure 1:
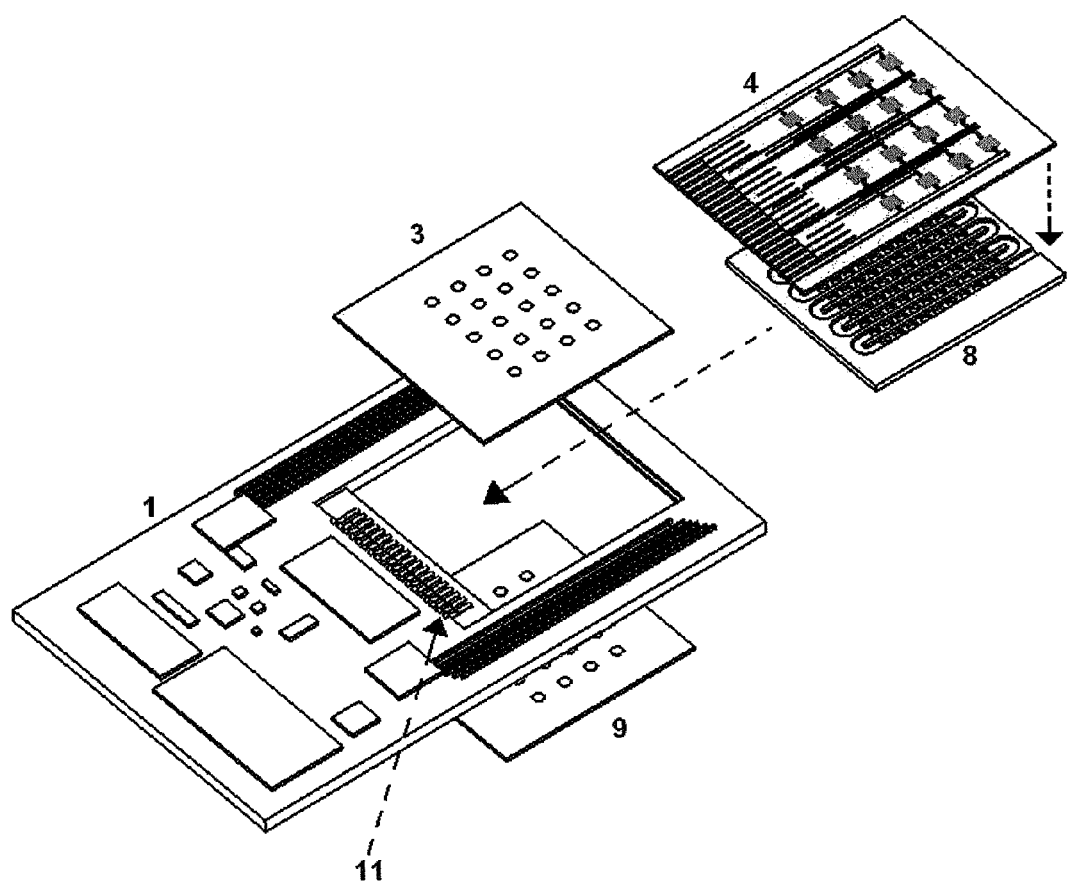

The sensor is in particular suitable for use in a method wherein a metal or other electrically conductive material is deposited to qualitatively or quantitatively detect an analyte of interest.

In general, the electrical detection system and the optical detection system are arranged such that a suitable change in the deposition can be detected. In particular, the electrical detection can be used in a similar way as described in Möller et al., i.e. in particular the method may comprise determining the enhancement time until a (characteristic) drop in resistance can be detected and use this as measure for the amount of the analyte, or in a way as described in any of the other publications identified herein.

As more of the metal or other conductive material is deposited, an optical characteristic, such as transmission, reflection or refraction typically changes. Thus, the optical detection is also particularly suitable to monitor the progress of the deposition before the drop in resistance occurs.

The inventors have further realised that accordingly the optical detection is particularly suitable to be used to detect the so-called percolation threshold of the deposition process, i.e. the moment at which sufficient deposition has formed between electrodes such that a continuous electrically conductive path has formed between electrodes of a detection cell in which an electrical and optical detection for an analyte of interest (or a reference) are performed. The determination of the percolation threshold may also be referred to as end-point detection. Thus, the invention allows to determine the end-point for the electrical detection on-line (during enhancement), whereby the method is simplified, compared to a known method wherein such detection in practice takes place off-line.

Further, a sensor according to the invention is relatively easy to miniaturise, even though, the sensor is provided with at least two fundamentally different detector types. Thus, the sensor may be or form part of a micro-structured device, such as a micro-chip or a foil shaped sensor.

Further, reliability of the sensor is in general enhanced, as the sensor provides at least two orthogonal detection techniques. In particular reliability may be enhanced with respect to improved sensitivity, improved detection limit, improved stability and/or a reduced risk of false positives/false negatives.

Sensitivity of a detection system, such as a sensor, is the extent to which the measured signal changes upon a particular change in the concentration or amount of the substance to be detected.

The detection limit is the lowest measurable concentration or amount of a substance. It is determined by the signal to noise ratio. In general, the detection limit for a particular substance is reached at a signal to noise ratio of 2 (if the noise is represented as peak to peak) or 4 (if the noise is represented as the root of the mean square noise (RMS noise)).

Stability is the extent to which a system is resistant to changes in the detection system, influences from the sample and influences from the environment. Accordingly, as a system is more stable, the noise will be less and/or fewer artefacts will occur in the measuring signal, such as spikes, base line drift and/or base line shifts.

The electrical detection system may suitably be based on the sensor described in Möller et al., in Diessel et al., in US 2003/0087277A1, in WO 2005/003772 A1 or in WO 00/39325. It generally comprises at least two electrodes 12, 13—which at least during deposition—are in contact with the contents of the fluid holder 8 (which may comprise a sample, which may comprise an analyte of interest, a liquid comprising reagents for the deposition of the metal or other conductive material.

At least during resistance or conductivity measurement, the electrodes are in electrical contact with a resistance meter or a conductivity meter (not shown). At the start of the measurement, the electrodes are usually spatially apart, to provide a gap 6, such that electrical resistance is high (or in other words, that conductivity is low, preferably essentially zero in the absence of a conductive liquid—such as a sample containing ions—between the electrodes). In case an electrically conductive material is deposited between the electrodes, the gap 6 may eventually be closed (deposition 7 in FIG. 2), resulting in an increased electrical conductivity.

The electrodes 12, 13 are preferably positioned essentially such that at least when using the sensor to detect an analyte—the electrodes are arranged such that the gap between the electrodes is at an angle of 45° to 135°, preferably of about 90°, with the light path (symbolised by the white arrows in FIG. 2) of the optical detection system.

The optical detection system is usually arranged to detect a change in the deposition of electrically conductive material. The system may be designed for transmissive, reflective, refractive or emissive (e.g. fluorescence, phosphorescence) detection.

The optical detection system usually comprises a light source and a photodetector. The optical detection system may be based on a optical detection system or a component thereof as described in the prior art, such as in WO 2005/015173 or WO 2005/01945, of which the contents are incorporated herein by reference.

Preferably the light source is a light emitting diode (LED), more preferably an organic LED (OLED). Such OLED is easy to employ in a microstructured device, as it is possible to provide OLEDs with a low thickness, length and/or width, e.g. by printing.

In particular, an organic light emitting diode (hereinafter OLED) is herein understood to mean a light emitting diode whose photoactive material (usually arranged in a layer) consists at least substantially of at least one (semi)conductive electroluminescent organic compound or composition. A polymeric light emitting diode (hereinafter called PLED) is herein understood to mean a light emitting diode whose photoactive layer consists at least substantially of at least one (semi)conductive electroluminescent organic polymer (including polymer mixtures) or at least one (semi)conductive organic polymer (including polymer mixtures) and at least one other organic compound (for instance a single compound), which is electroluminescent.

Preferred electroluminescent compounds are polyarylenes, more preferably poly(paraphenylene vinylene) compounds (PPV compounds), polyacetylenes, polyanilines, polythiophenes, polyfluorenes, polyvinylcarbazoles, copolymers thereof and mixtures thereof.

The photodetector preferably comprises a photodiode, in particular an organic photodiode. An organic and polymeric photodiode, respectively (hereinafter called photodiode) is herein understood to mean a photodiode whose photoactive material (usually arranged in a layer) consists at least substantially of at least one (semi)conductive organic compound (including a composition thereof), and of at least one (semi) conductive organic polymer (including a composition thereof), respectively.

The photodiode can comprise a photo-active material which exhibits photoconduction when it is under an electric potential.

Advantageously, the photodiode is a photovoltaic cell, which, without an electric potential present, exhibits photoconduction and is capable of converting photon energy into electric energy. In such a cell, as electron-donating material and preferably also as electron-accepting material, an organic compound, more preferably an organic polymer, is present.

Electron-donating and electron-accepting material can be mixed or be present in separate layers.

Preferably, a photodiode is selected from the group of photodiodes having in the photoactive layer a polymer selected from the group consisting of polyarylene compounds, poly(paraphenylene vinylene) compounds, polyfluorene compounds, polyacetylene compounds, polythiophene compounds, polypyrroles, polyanilines, including derivatives of said polymers (in particular alkyl, aryl and alkoxy derivatives), copolymers of said polymers and said polymers which have been derivatized with a dye. In a photovoltaic cell, such polymers have been found very suitable as electron-donating compound.

Figure 2:
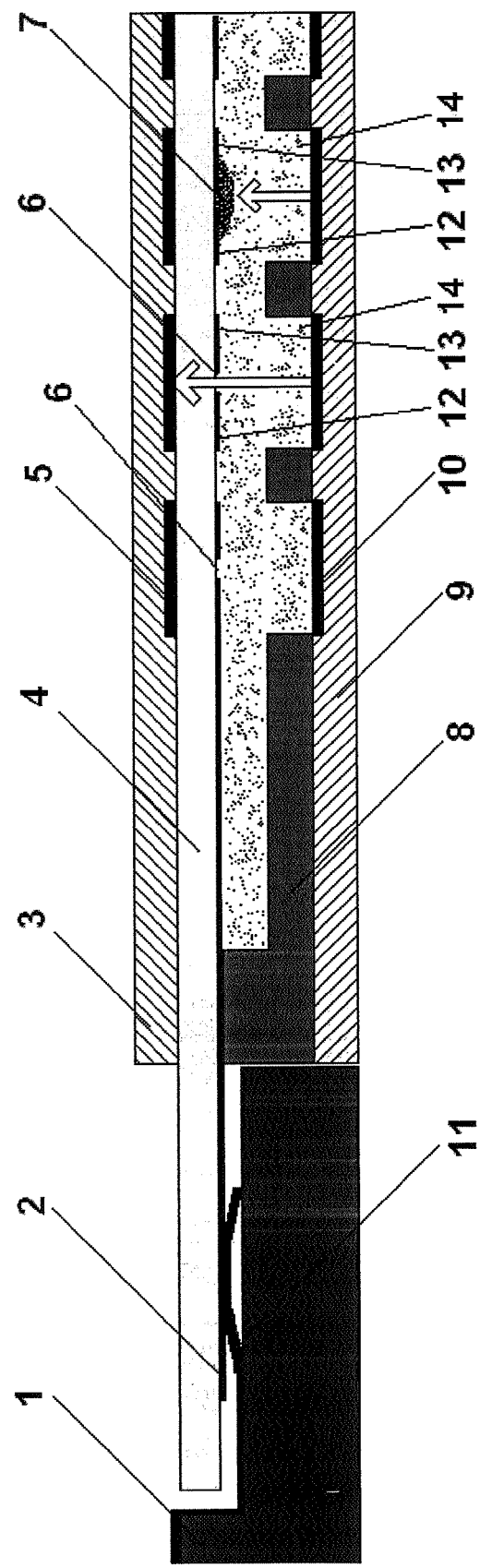
FIG. 2 shows a cross-sectional view of a sensor according to the invention.

In an advantageous embodiment, e.g. as shown in FIGS. 1 and 2, a micro-fluidic structure 8 may provide a holder for one or more samples. Such structure comprises one or more recesses in a substrate, wherein one or more samples can be held. The design of the structure and the detection systems allows the sample(s) to be in physical contact with (a gap between) electrodes of the electrical detection system.

As shown in the FIGS. 1 and 2, a plurality of detection cells 14 (each comprising at least two electrodes, a light source and a photodetection unit) may be interconnected, via a channel through which a fluid can flow. Thus a single sample may be introduced into the structure, in case different detection cells are used, which may in particular differ in that different probes may be present in different cells (see below) and/or in that a light source emitting a different light with a different (maximum) wavelength is present, a plurality of analytes in the same sample may be analysed simultaneously. The design of a micro-fluidic structure as shown also facilitates applying reagents and/or washing fluids, compared to a titre-plate like design of the fluid holder, wherein the different detection cells are not interconnected.

In a preferred embodiment, the sensor is provided with a probe for the analyte of interest, such that it is in contact with the analyte during use. Preferably, the probe is present in gap 6 between the electrodes 12,13. A probe is a binding site for a specific analyte or for a specific group of analytes (see also below).

The sensor may advantageously be provided with a controller (adapted) for regulating the electrical detection system, dependent on the detection signal originating from the optical detection system and/or for regulating the optical detection system, dependent on the detection signal originating from the electrical detection system.

In a preferred embodiment (shown in FIGS. 1 and 2) the sensor comprises a microfluidic structure as a fluid holder 8, forming part of a plurality of detection cells 14 for measuring conductivity or resistance, each detection cell 14 comprising at least two electrodes 12, 13 for measuring electric conductivity or resistance over gap 6 in said cells. Thus, a difference can be measured between a sample wherein no deposition (maintaining a gap 6 as shown in FIG. 2, middle detection cell 14 of the fully shown cells) or insufficient deposition takes place and a sample wherein sufficient deposition takes place to fill the gap (deposition 7, as shown in FIG. 2).

Usually the sensor comprises a read-out system 1, which can hold the fluid holder 8.

Figure 3:
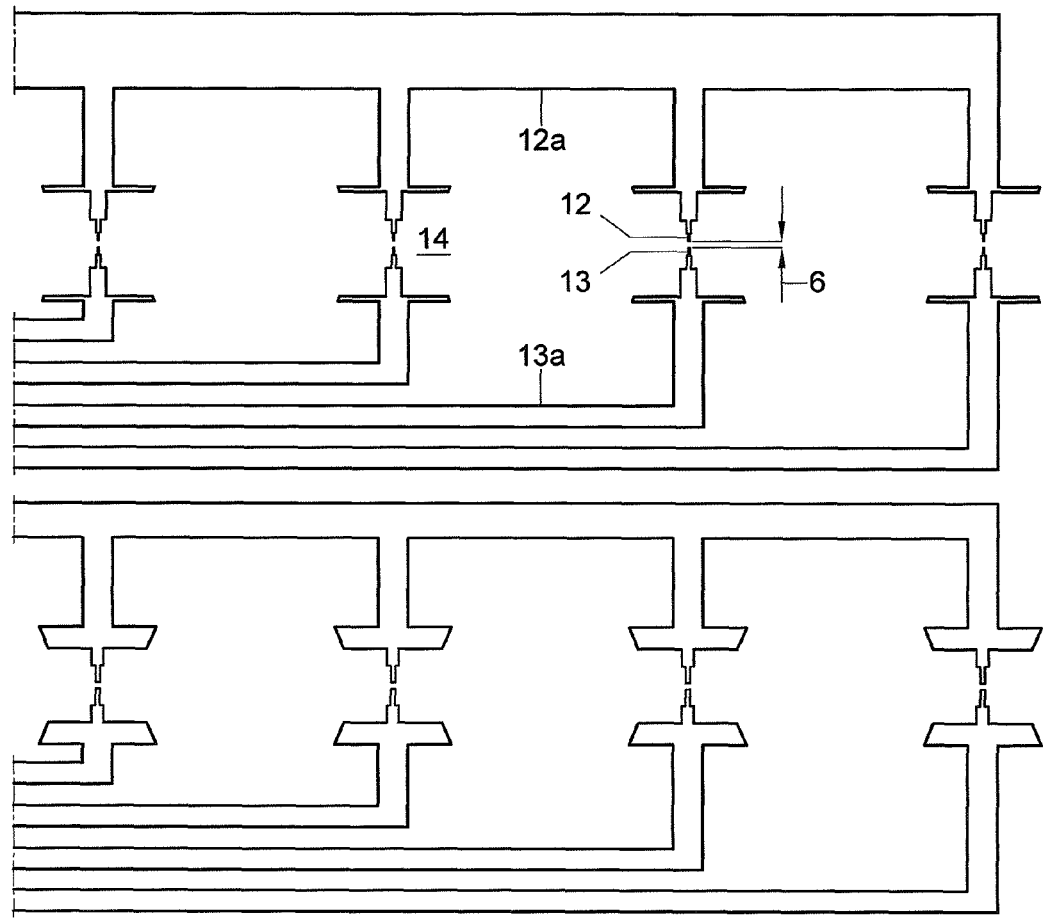
FIG. 3 shows a detail of an array of electrical conductivity/resistance detection cells.

At least during use (at least when applying a sample and if desired during an enhancement step for depositing an electrically conductive material), the fluid holder 8, usually is positioned such that the contents of the fluid holder (sample, reagents for allowing enhancement) are in contact with (a gap between) the electrodes 12,13. The electrodes may be suitable provided as an array 4. FIG. 3 shows a part of such an array 4. Herein the electrodes 12, 13 are connected via electroconductive structures 12a, 13a. When positioned for use in the read-out system 1, structures 12a, 13a are in electrical contact with the connector 11 via electrical contact points 2 (shown in FIG. 2).

The read-out system 1 of a sensor according to the invention usually comprises an electric conductivity or resistance meter for measuring the conductivity or resistance between electrodes of a detection cell, a calculator for processing the measurement signals and/or a display for showing a result (not shown in detail in the Figures). These may be assembled on a printed circuit board. Preferably, at least the fluid holder 8 and/or the detection system for measuring electrical conductivity of resistance, such as array 4, are disposables. These can usually be removed from the sensor and replaced without having to disassemble the remainder of the sensor. To this purpose, the detection system for measuring electrical conductivity or resistance, such as array 4 is advantageously provided with a connector 11 for providing electrical contact between (conductivity or resistance meter of) the read-out system and the electrodes 12 and 13.

The read-out system 1, further usually comprises a light-source 10, in particular a LED, more in particular an organic LED, and an optical detector 5—in particular a photodiode, more in particular an organic photodiode—of the optical detection system. It is also possible to provide the light source 10 and/or the optical detector 5 as replaceable parts. In particular OLEDs and organic photodiodes are useful for this embodiment, as they can be made cheaply, such that economic use thereof as disposables is possible.

In an advantageous embodiment, the light source 10, and the optical detector 5, are pixelated. Organic LEDs and organic detection photodiodes are in particular easy to provide as pixels, e.g. by applying layers manufacturing the LED and/or detection photodiodes by printing or another suitable technique in a patterned way on a substrate, thereby forming a patterned LED array 9 respectively a patterned photodiode array 3.

At least during use, the light source 10 and optical detector 5 are preferably positioned essentially parallel to each other at opposite sides of the (gap between) the electrodes 12 and 13, for efficient transmissive detection of light emitted from the light source 10 by optical detector 5.

As indicated above, a microfluidic device is suitable as a fluid holder. Such system is advantageous as it allows miniaturisation of the sensor. Microfluidic devices are microstructured devices capable of holding and/or manipulating a fluid. Such devices typically comprise a pattern (structure) of one or more recesses (such as one or more channels and/or one or more cavities) of which at least one dimension is of a micrometer scale (typically about 1 to 1000 μm). The one or more recesses usually have a depth and/or width of in the range of 1-1000 μm. In particular the depth and/or width may be 200 μm or less, more in particular 50 μm or less. The length of the recess(es) may be in the range of 1-1000 μm or higher. The upper limit is determined by the size of the device. One or more recesses having other dimensions may be present (in addition). In accordance with the invention, at least during use, the microfluidic device 8 is preferably covered with an array 4 of conductivity/resistance detection cells 14, such that (the contents of the) fluid holders are in direct contact with the electrodes 12, 13.

The sensor may comprise a plurality of detection cells 14 wherein different cells are provided with different probes, selective for a different analyte. Thus, a single sensor can be used for simultaneously screening for the presence of a plurality of different analytes of interest in a single sample or for simultaneous quantitative analysis of a plurality of analytes.

As described above, the invention further relates to a method for detecting an analyte, comprising applying a sample to a fluid holder of a sensor according the invention, measuring an optical property in the fluid holder with the optical detection system and measuring the conductivity or resistance with the electrical detection system. A method according to the invention usually comprises deposition of a reagent, dependent upon the presence of an analyte of interest. Suitable analytical techniques, such as suitable deposition techniques are known in the art, e.g. from the above mentioned publications by Möller et al., by Diessel et al., in US 2003/0087277A1, in WO 2005/003772 A1 or in WO00/39325 of which the contents with respect to suitable deposition techniques are incorporated herein by reference. The skilled person will be able to select suitable conditions for other analytes, based on the information disclosed herein, in any of the cited prior art, common general knowledge and optionally some routine testing.

In a preferred method of the invention a sample which is checked for the presence of an analyte of interest is provided in a fluid holder and contacted with a probe to which the analyte can bind. The probe is usually immobilised in a gap between at least two electrodes forming part of the electrical detection system.

For allowing or enhancing deposition of an electrically conductive material, the probe (comprising analyte, if present in the sample) may be contacted with a deposition nucleus such as a nanoparticle, which may be of the same material as the material that is to be deposited). This facilitates deposition. The nucleus is usually provided with a binding site to bind to analyte bound to a probe. Alternatively one may provide the nucleus with a binding site to a probe to which no analyte has bound, e.g. for use in a competition assay.

It is also possible to use a catalyst, such as an enzyme, capable of catalysing the deposition. In particular suitable to that purpose is a peroxidase. Other enzymes which may be used include phosphatases (in particular alkaline phosphatase) and oxidases, such as glucose oxidase. The catalyst is usually provided with a binding site to bind to either analyte bound to a probe.

The deposition nucleus or catalyst may be provided before, during or after the analyte (if present) has been allowed sufficient time to bind to the probe. After the analyte has been allowed sufficient time to bind to the probe (if an analyte is present that can bind), conditions are provided such that an electrically conductive deposit is allowed to be formed in the presence of nuclei that may be present.

Suitable probes for a specific analyte of interest or a suitable method of providing a probe for a specific analyte of interest are known in the art. For instance, an antibody capable of binding the analyte may be used as a probe. An antibody is in particular useful for the binding of oligopeptides, polypeptides or other analytes against which a selective antibody can be provided. Suitable methods to provide such antibodies are generally known in the art for both analytes that are immunogenic antigens and haptens that are not immunogenic per se are generally known in the art.

In particular for (oligo/nucleotides)nucleotides a probe may be an (oligo/poly)nucleotide comprising a sequence that is essentially complementary to at least a part of the analyte of interest. Further, nucleotides, such as oligo- or polynucleotides, may also be useful as a probe for a polypeptide.

Further, a receptor molecule for a specific compound may be used. Receptor molecules may for instance be specific molecules for recognising a specific compound, which molecules can be found at cell membranes, e.g. specific (glyco) proteins.

Suitable deposition nuclei include those described in the prior art identified herein. In particular, suitable deposition nuclei comprise an electrically conductive material comprising a metal. Also suitable are non-metal deposition nuclei like graphite or organic polymers. In particular, also suitable deposition nuclei comprise nuclei with surfaces that facilitate deposition of conductive deposits from solution, at least in the presence of a suitable catalyst, preferably an enzyme.

In a preferred embodiment said deposition nucleus comprises gold, silver, iron, copper, nickel or mixtures comprising of one or more of said metals. Preferred deposition nuclei may also comprise non-metal substances such as polymer beads with catalytically active substances on their surface. In an especially preferred embodiment said deposition nucleus comprises gold. Gold and particularly gold colloids are particularly suited because its surface is catalytically active, as described above.

The deposition nucleus comprises a particle comprising the material on which said deposit is to be formed. In particular, suitable sizes for the particles range from 0.1 nm to 5 μm. Preferably, the size of the particles ranges from 0.8 nm to 250 nm.

Suitable deposition conditions can be based on prior art technology. Such conditions may in particular be realised by providing the fluid holder with reducible metal ions or reducible ions of another material that is electrically conductive (such as a metalloid) and with a suitable reducing agent to reduce the ions to a non-ionic (such as metallic) state, thereby selectively forming an electrically conductive deposition in gap 6 wherein an analyte and a nucleus are present.

Metal ions are particularly preferred because after reduction these generally provide a deposition that has a good conductivity and a much lower transmission for UV, VIS or IR-light, thus making it particularly suitable for use in a combined detection technique making use of both electrical (conductivity/resistance) and optical (transmission/absorbance or reflection) detection. In particular, a metal ion may be present selected from copper, silver, gold, platinum, nickel, lead, mercury and metal ions that are at least as easy to reduce as any of these. Suitable reducing agents for a specific reducible ion are generally known in the art, e.g. from US 2003/008277 A1, in particular paragraph [0064] of which the contents are incorporated by reference.

In a preferred embodiment, a sensor according to the invention is used to determine the presence of an analyte of interest qualitatively and/or quantitatively using a method comprising
  contacting a surface comprising an immobilized probe for an analyte of interest with a sample, which may comprise the analyte, under conditions allowing binding of the probe and the analyte,
  providing a deposition nucleus or catalyst capable of binding either to bound analyte or to a probe to which no analyte is bound, preferably to bound analyte;
  subsequently performing an enhancement step on said surface by depositing an electrically conductive deposit at or near the probe (between electrodes of a detection cell);
  determining an optical characteristic, in particular UV/VIS/IR transmission, absorbance, extinction, or reflection, at a suitable wavelength (such as at or near a maximum in the absorption spectrum of the deposited material); and
  determining the electrical resistance or conductivity of said surface.

Preferably, the fluid holder is rinsed with a rinsing fluid between application of sample and nucleation reagent and between sample and deposition reagent (e.g. water or another fluid which is free of the analyte and other constituents which may adversely affect the binding of probe with analyte or nucleation agent with analyte, to remove unbound constituents).

Preferably, at least the part of the electrical detection system wherein the electrical detection takes place (such as the space between electrodes between which resistance or conductivity is measured) is dried before measuring the conductivity or measurement to determine the presence of the analyte. It is contemplated that thus a more accurate result can be obtained, as the presence of a liquid during the measurement may affect the conductivity/resistance. E.g. the fluid may contribute to conductivity and/or the fluid may cause swelling of the deposited conductive material, affecting conductivity of the material. Drying may in particular be carried out using a gas, such as air, nitrogen, a noble gas or another inert gas. The gas may for instance be suitably flown through a channel in a microfluidic device which is in fluid communication with electrodes (and gaps between the electrodes) of the electrical detection system.

Optionally, the electrical resistance/conductivity and/or optical characteristic of said surface are compared with a reference and/or standards for calibration purposes.

A sensor according to the invention may in particular be used in a method for detecting binding of members of a specific binding pair (analyte and probe) comprising providing a first member of said binding pair coupled to a deposition nucleus (analyte) and specifically binding said first member to a surface-immobilized second member (probe) of said pair and determining the electrical resistance of said surface, wherein after binding of the members on said surface an electrically conductive deposit is formed on said surface under conditions that allow said deposit to be formed specifically on said nucleus or deposit formed.

In a preferred method according to the invention, the detection signal of the optical detection system is used to determine at which moment in time or during which period in time the electrical measurement is carried out for detecting the analyte. Usually, at a specific moment in time during depositing silver or another conductive material from an (electro-less) deposition fluid, the system passes a percolation threshold, which is accompanied by a marked increase of the electrical conductivity. Complementary to the electrical detection of the percolation threshold, optical characterization will provide a second path to assess the deposition process. In principle, the optical method of detecting the percolation threshold will yield substantially more information, since it already provides a signal even when a direct electrical current path is not available. In particular, the optical detection allows automatic determination of the percolation point, and can thereby trigger the electrical detection.

The invention claimed is:

1. Sensor for the detection of an analyte, comprising a fluid holder, an optical detection system for carrying out an optical detection at the fluid holder and an electrical detection system for measuring electric conductivity or resistance inside the fluid holder, wherein the sensor is provided with a controller for regulating the electrical detection system, dependent on the detection signal originating from the optical detection system and/or for regulating the optical detection system, dependent on the detection signal originating from the electrical detection system.

2. Sensor according to claim 1, wherein the electrical detection system comprises at least two electrodes, which are at least prior to use spatially apart, for measuring the electric conductivity or resistance.

3. Sensor according to claim 2, wherein a probe for an analyte of interest is present between two electrodes of the electrical detection system.

4. Sensor according to claim 2, wherein the electrodes are arranged such that at least when using the sensor to detect an analyte—the space between the electrodes is at an angle of 45°-135°, with the light path of the optical detection system.

5. Sensor according to claim 1, wherein the sensor comprises a fluid holder, defining a plurality of detection cells, of which at least a number are each provided with: at least two electrodes for measuring electric conductivity or resistance in the detection cell provided with said electrodes, a light-source and an optical detection unit, the sensor further comprising a read-out system, which can hold the fluid holder, the read out system comprising an electric conductivity or resistance meter for measuring the conductivity or resistance (in the gap) between two electrodes of a detection cell and a connector for electrically conductively connecting the meter with the electrodes, the read-out system further comprising a module for measuring the output of the optical detection unit.

6. Sensor according to claim 1, wherein the sensor is a micro-structured device.

7. Sensor according to claim 5, wherein the light source comprises a LED.

8. Sensor according to claim 5, wherein the optical detection unit comprises a photodiode.

9. Sensor according to claim 1, wherein the controller is configured to regulate the electrical detection system dependent on the detection signal from the optical detection signal, and wherein the optical detection signal that regulates the electrical detection system is the detection signal that indicates a percolation threshold.

* * * * *

UNITED STATES PATENT AND TRADEMARK OFFICE
CERTIFICATE OF CORRECTION

PATENT NO.      : 8,623,283 B2                                                      Page 1 of 1
APPLICATION NO. : 12/668235
DATED           : January 7, 2014
INVENTOR(S)     : Van Breemen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 976 days.

Signed and Sealed this
Twenty-second Day of September, 2015

Michelle K. Lee
*Director of the United States Patent and Trademark Office*